United States Patent
Ko et al.

(10) Patent No.: US 9,149,338 B2
(45) Date of Patent: Oct. 6, 2015

(54) END EFFECTOR AND REMOTE CONTROL APPARATUS

(71) Applicant: SAMSUNG ELECTRONICS CO., LTD., Suwon-si, Gyeonggi-do (KR)

(72) Inventors: Won Jun Ko, Yongin-si (KR); Jung Yun Choi, Seoul (KR); Se Gon Roh, Suwon-si (KR); Tae Sin Ha, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 84 days.

(21) Appl. No.: 13/886,751

(22) Filed: May 3, 2013

(65) Prior Publication Data

US 2014/0330073 A1    Nov. 6, 2014

(30) Foreign Application Priority Data

May 15, 2012 (KR) .................. 10-2012-0051307

(51) Int. Cl.

| G06F 19/00 | (2011.01) |
| A61B 19/00 | (2006.01) |
| A61B 17/04 | (2006.01) |
| A61B 17/062 | (2006.01) |
| A61B 17/00 | (2006.01) |

(52) U.S. Cl.
CPC ......... *A61B 19/2203* (2013.01); *A61B 17/0469* (2013.01); *A61B 17/062* (2013.01); *A61B 2017/00212* (2013.01); *A61B 2019/2292* (2013.01); *A61B 2019/465* (2013.01)

(58) Field of Classification Search
CPC .... B25J 9/1697; B25J 11/008; B25J 19/0091; B25J 19/023; B25J 19/06; A61B 19/2203; A61B 2019/2223; A61B 2017/00477; A61B 19/5212; A61B 2019/2234
USPC ................ 700/245, 259, 248; 901/1; 345/15; 701/23; 606/130; 600/102; 318/568.11
See application file for complete search history.

(56) References Cited

U.S. PATENT DOCUMENTS

| 4,813,844 | A  | * | 3/1989 | Torii et al. ..................... 414/730 |
| 6,377,011 | B1 |   | 4/2002 | Ben-Ur |
| 6,879,880 | B2 |   | 4/2005 | Nowlin et al. |
| 8,005,571 | B2 | * | 8/2011 | Sutherland et al. ........... 700/248 |
| 8,374,723 | B2 | * | 2/2013 | Zhao et al. .................... 700/259 |
| 8,396,598 | B2 | * | 3/2013 | Sutherland et al. ........... 700/264 |

(Continued)

FOREIGN PATENT DOCUMENTS

| JP | 2003-79638 | 3/2003 |
| KR | 10-2010-0025092 | 3/2010 |

*Primary Examiner* — McDieunel Marc
(74) *Attorney, Agent, or Firm* — Harness, Dickey & Pierce, P.L.C.

(57) ABSTRACT

An end effector includes a tip part having a deformation member that is physically changed due to contact with an object, a gauge display part configured to display gauge information according to a physical change of the deformation member, and a connecting rod part connected to the tip part and configured to operate the tip part. A manipulator including an end effector configured to display physical information, which varies according to an object making contact with a tip part, on a gauge display part, an endoscope configured to obtain an image of the tip part of the end effector and an image of the gauge display part, and a control part configured to control transmission of the image obtained by the endoscope, and to control operations of the tip part and the endoscope.

15 Claims, 20 Drawing Sheets

(56) References Cited

U.S. PATENT DOCUMENTS

| | | | |
|---|---|---|---|
| 8,594,841 B2* | 11/2013 | Zhao et al. | 700/245 |
| 2004/0111183 A1* | 6/2004 | Sutherland et al. | 700/245 |
| 2007/0032906 A1* | 2/2007 | Sutherland et al. | 700/248 |
| 2008/0161677 A1* | 7/2008 | Sutherland et al. | 600/417 |
| 2008/0161830 A1* | 7/2008 | Sutherland et al. | 606/130 |
| 2009/0005734 A1 | 1/2009 | Herbette et al. | |
| 2009/0245600 A1* | 10/2009 | Hoffman et al. | 382/128 |
| 2009/0248036 A1* | 10/2009 | Hoffman et al. | 606/130 |
| 2010/0063630 A1* | 3/2010 | Sutherland et al. | 700/264 |

* cited by examiner

END EFFECTOR AND REMOTE CONTROL APPARATUS

CROSS-REFERENCE TO RELATED APPLICATIONS

This application claims the benefit of Korean Patent Application No. 10-2012-0051307, filed on May 15, 2012, in the Korean Intellectual Property Office, the disclosure of which is incorporated herein by reference.

BACKGROUND

1. Field

One or more embodiments relate to an end effector capable of improving the accuracy of detection of physical information, and a remote control apparatus having the same.

2. Description of the Related Art

A remote control apparatus is an apparatus including a master part and a slave part, and remotely controls the slave located at a remote site by use of the master part. The master part controls the operation of the slave part based on various types of physical information, such as force, tactile sensation, temperature, humidity, and illuminance that are detected from the slave part.

Examples of the remote control apparatus include a surgery robot, a hazardous material handling robot, a patrol robot, a military robot and an aerospace remote apparatus.

The surgical robot represents a robot that performs a treatment or a surgery on an affected area by moving a surgical instrument according to a command by a user, and includes a console corresponding to a master part, a manipulator and an end effector that each correspond to a slave part.

The surgery performed by the surgery robot includes a minimal invasive surgery in which a size of an affected area is minimal, and a robotic surgery. The minimal invasive surgery, different from an open surgery having an abdomen entirely open to perform a surgery, makes a few small incisions through an abdomen and the abdomen is filled with gas to create a surgical space, and a laparoscope and a surgical end effector are inserted through the incision such that a surgery is performed using the surgical end effector while observing an internal image of the abdomen.

The minimal invasive surgery generally involves less post-surgical pain while enabling an early recovery of intestinal movement and of the ability to ingest food earlier relative to open surgeries. In addition, the minimal invasive surgery requires shorter length of hospitalization, and thereby a return to a normal condition is faster. Furthermore, since an area of an incision from the minimal invasive surgery is small, an aesthetic effect is superior. Thus, the minimal invasive surgery is being applied in numerous types of surgeries, including gall bladder removal surgery, prostate cancer surgery, hernia correction surgery, etc., and is increasingly being used in the medical field.

The minimal invasive surgery, however, accompanies difficulty in controlling a surgical end effector and in moving an instrument through an incision. In addition, with respect to minimal invasive surgery, the position displayed through an image to a user, when compared to the actual position inside an abdomen, is reversed both vertically and horizontally. Therefore, a skilled surgeon and medical staff are needed.

The weaknesses of minimal invasive surgery may be overcome in part by performing a surgery using a da Vinci robot. Here, a da Vinci robot is configured to deliver a dimensional image, which is expanded by 10 to 15 times in size without a vertical/horizontal reversal, to a user, and is also configured to deliver the movement of a user precisely to a manipulator and a surgical end effector.

The surgical robot as the above is not provided with a feedback function of a force and a tactile sensation. Accordingly, a user, that is, a surgeon, has difficulty in recognizing a force applied to a surgical end effector during surgical suturing. As a result, a surgical thread is excessive pulled and broken during the suturing, or an excessive force is applied to intestine tissues and thus the intestine tissue may be damaged.

In this regard, a technology is developed to receive a feedback of force and tactile sensation information by use of a sensor, such as a strain gauge, included in a surgical end effector, and control the surgical end effector based on the feedback force and tactile information.

In this case, the detected force information is converted into an electric signal and is transmitted to a console. In a process of converting the force information, that is, physical information, into an electric signal, noise is added so that the reliability of the detected force information is lowered.

In addition, a process of transmitting and receiving force information between a console and an end effector is additionally required, and thus the network traffic is increased. In addition, a time synchronization between the detection time of force information and the display time of force information is required, and also an image of the force information and an image of the surgical end effector need to be individually checked during a surgery operation.

In addition, at the time of displaying an image of the force information at a surrounding area of an image about the surgical end effector during a surgery operation, an additional program for an augmented reality (AR) is required to be installed at a surgical robot.

SUMMARY

The foregoing described problems may be overcome and/or other aspects may be achieved by one or more embodiments of an end effector that may display physical information about an object according to contact with an object.

The foregoing described problems may be overcome and/or other aspects may be achieved by one or more embodiments of a remote control apparatus that may simultaneously obtain a display image of physical information about an object according to contact with the object and an image of the tip part of an end effector, when the tip part is brought into contact with the object.

The foregoing described problems may be overcome and/or other aspects may be achieved by one or more embodiments of a remote control apparatus having a console that may output an image of a tip part of an end effector, which is transmitted from the outside, and an image of physical information according to contact with an object.

In accordance with one or more embodiments, an end effector may include, for example, a tip part, a gauge display part and a connecting rod part. The tip part may have a deformation member that may be physically changed due to contact with an object. The gauge display part may be configured to display gauge information according to a physical change of the deformation member. The connecting rod part may be connected to the tip part and configured to operate the tip part.

The end effector may further include a fluid and a connection pipe. The fluid may be filled in the deformation member. The connection pipe may be connected between the deformation member and the gauge display part. The fluid may move between the deformation member and the guide display part through the connection pipe.

The fluid may move from the deformation member to the gauge display part by an amount corresponding to a force applied to the tip part at the time of making contact with the object.

The tip part may include a body part and a contact member. The body part may be configured to accommodate the deformation member and the connection pipe. The contact member may be connected to the body so as to make contact with the deformation member, and may be configured to make contact with the object.

The contact member may be movably connected to the body. The deformation member may be physically changed according to a movement of the contact member.

The tip part may further include an elastic member disposed inside the body, and configured to provide the contact member with a restoring force.

The gauge display part may include a cylinder and a piston. The cylinder may be connected to the connection pipe. The piston may be disposed inside the cylinder and configured to reciprocate inside the cylinder in response to a movement of the fluid.

The cylinder may be formed of transparent material.

The cylinder may include a scale corresponding to the gauge information.

The fluid may have a color.

The gauge display part may include a dial gauge configured to rotate a pointer in response to the reciprocating movement of the piston.

The cylinder may include semi-transparent coating layers each having a different color corresponding to the gauge information.

The gauge display part may include a position detection part, a control part and an indicator. The position detection part may be configured to detect a position of the piston corresponding to the gauge information. The control part may be configured to convert the detected position to an electric signal, and to control displaying of the electric signal. The indicator may be configured to display the gauge information by use of an electric signal.

The indicator may be an RGB LED that changes a color thereof based on the converted electric signal.

The indicator may include a color panel and an indication bar. The color panel may be configured to display a caution level through different color bands. The indication bar may be configured to move to a position corresponding to one of the different color bands according to a command by the control part so that the indication bar points at the one of the different color bands corresponding to the converted electric signal.

The indicator may include a plurality of LEDs each having a different color, and may turn on at least one of the plurality of LEDs based on the converted electric signal.

The indicator may include at least one of a seven segment display configured to display a numeric value corresponding to the converted electric signal.

The gauge display part may be disposed at the connecting rod part.

The fluid may change a color or a volume thereof according physical information including one among temperature, humidity and illuminance.

In accordance with another aspect of the present disclosure, a remote control apparatus may be provided with a manipulator that may include, for example, an end effector, an endoscope and a control part. The end effector may be configured to display physical information, which varies according to an object making contact with a tip part, on a gauge display part. The endoscope may be configured to obtain an image of the tip part of the end effector and an image of the gauge display part. The control part may be configured to control transmission of the image obtained by the endoscope, and to control operations of the tip part and the endoscope.

The remote control apparatus may further include a display part configured to display an image being transmitted from the control part.

The remote control apparatus may further include, for example, a first arm to which a connecting rod part of the end effector, and a second arm to which the endoscope is connected. The control part may control movements of the first arm and the second arm.

The end effector may include a first tip part and a second tip part that may be configured to grip the object.

At least one of the first tip part and the second tip part may include, for example, a body, a deformation member, a contact member, and a connection pipe. The deformation member may be accommodated in the body and may be filled with a fluid. The contact member may be movably installed at the body, and may be configured to deform the deformation member in response to a force applied to the object at the time of making contact with the object. The connection pipe may be connected between the deformation member and the gauge display part. The fluid may move between the deformation member and the gauge display part through the connection pipe.

The tip part may further include an elastic member disposed inside the body and configured to provide the contact member with a restoring force.

The gauge display part may include, for example, a cylinder and a piston. The cylinder may be connected to the connection pipe. The piston may be disposed inside the cylinder and may be configured to reciprocate inside the cylinder in response to movement of the fluid.

The gauge display part may include, for example, a position detection part, a control part and an indicator. The position detection part may be configured to detect a position of the piston. The control part may be configured to convert the detected position into an electric signal. The indicator may be configured to display the physical information in an electric manner according to a command by the control part.

In accordance with one or more embodiments, a remote control apparatus may include, for example, a communication part, a control part and a console. The communication part may be configured to perform a communication with a manipulator. The control part may be configured to control such that an image being transmitted from the manipulator is displayed. The console may have an output part configured to display the image. The image may include an image of a tip part of an end effector and an image of gauge information of the end effector.

The console may be configured to transmit an operation control signal of the end effector to the manipulator.

The console may be configured to display an enlarged view of the image of the gauge information at a periphery of the image of the end effector.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
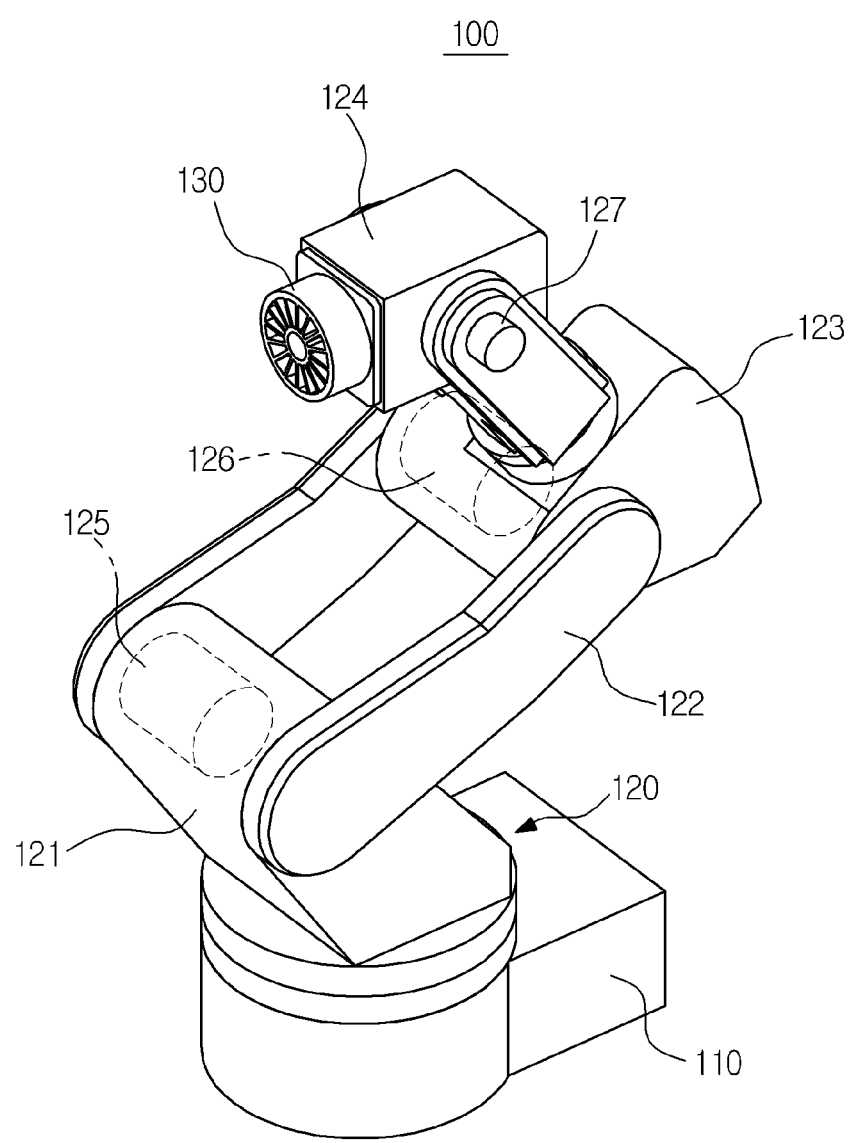
FIG. 1 is an exemplary view illustrating a manipulator of a remote control apparatus in accordance with one or more embodiments.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

Figure 2:
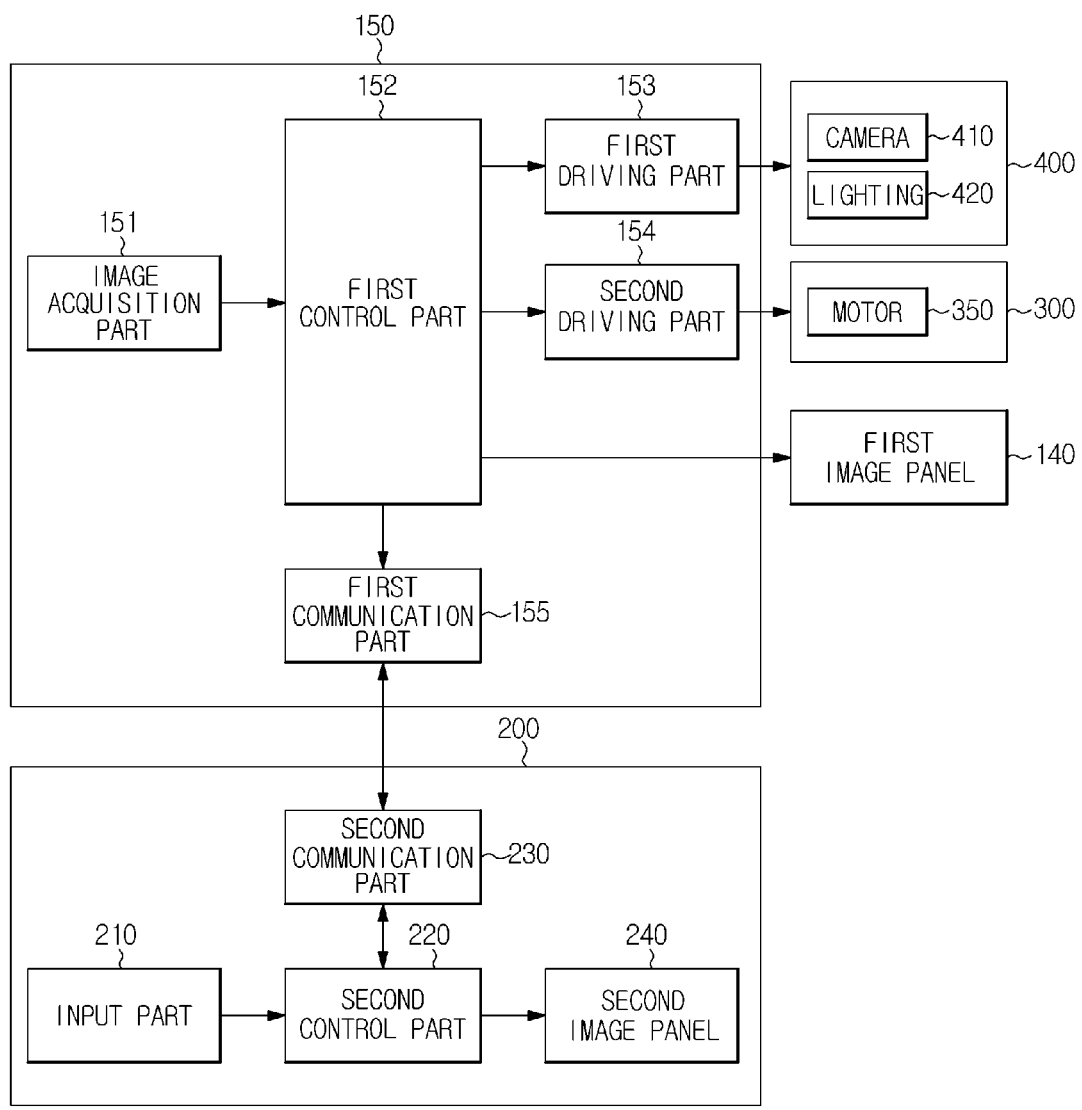
FIG. 2 is a control block diagram of a remote control apparatus in accordance with one or more embodiments, such as the remote control apparatus of FIG. 1.

FIG. 1 is an exemplary view illustrating a manipulator of a remote control apparatus in accordance with one or more embodiments. FIG. 2 is a control block diagram of a remote control apparatus in accordance with one or more embodiments, such as the remote control apparatus of FIG. 1.

Hereinafter, a surgical robot will be described as an example of a remote control apparatus.

A surgical robot may include a manipulator 100 that may be installed at a surgical table or adjacent to a surgical table, and a console 200 for a user to observe an affected area and control the manipulator 100.

The manipulator 100 may be mechanically and electrically connected to an end effector 300 configured for a treatment or a surgery, or an endoscope 400 configured to obtain images of an effected area, the end effector 300 and a surrounding environment.

Referring to FIG. 1, the manipulator 100 may include, for example, a body 110, an arm 120 that may be movably mounted on the body 110, and a coupling member 130 to which the end effector 300 or the endoscope 400 may be detachably coupled. The arm 120 may be provided in plurality thereof.

The arm 120 may be divided into a surgical arm to which the end effector 300 may be detachably coupled, and an endoscope arm to which the endoscope 400 may be detachably coupled.

The arm 120 may include a plurality of links and at least one joint so as to perform a multiple axes movement.

For example, the arm 120 may include a plurality of links 121, 122, 123 and 124, and a joint may be provided between adjacent links among the plurality of links 121, 122, 123 and 124 while possibly including a motor, so that each link may be rotatable.

The arm 120 may include, for example, a first link 121 connected to the body 110, a second link 122 connected to the first link 121 through a joint, a third link 123 connected to the second link 122 through a joint, and a fourth link 124 connected to the third link 123 through a joint and to which the coupling member 130 may be mounted. The arm 120 may include motors 125, 126 and 127 that may be configured to apply a moving force to each link such that each link may be movable.

In detail, the arm 120 may include, for example, a first motor 125 that may be installed inside the first link 121 that may rotate other links 122, 123 and 124, a second motor 126 that may be installed inside the second link 122 that may rotate the third and fourth links 123 and 124, and a third motor 127 that may be installed inside the third link 123 that may vertically move the fourth link 124.

That is, the arm 120 may respectively rotate the plurality of motors according to a command by the console 200, so that the position of the end effector 300 may be adjusted. The arm 120 may enable free movement, so that a command by an operator, that is, a surgeon may be delivered to the end effector 300.

The coupling member 130 may be located, for example, at the fourth link 124. An end effector 300 or an endoscope 400, for example, may be detachably coupled to the coupling member 130. An end effector 300 or an endoscope 400 coupled to the coupling part 130 may be electrically connected to a controller 150.

The manipulator 100 may further include a first image panel 140 to display an image obtained through the endoscope 400.

The first image panel 140 may be a device provided, for example, not for an operator, that is, a surgeon, but for an assistant, and may be configured to output images of the affected area, the end effector to treat the affected area and the surrounding area in the form of a two-dimension image or a three dimension image.

In addition, the manipulator 100 may further include buttons or switches on the body 110 to directly receive an operation command from an assistant.

The manipulator 100 may further include the controller 150 configured to perform a communication with the console 200 and control the operations of the arm 120, the end effector 300, and the endoscope 400 in response to a command being transmitted from the console 200.

Hereinafter, the control configuration between the controller 150 of the manipulator 100 and the console 200 will be described with reference to FIG. 2.

Referring to FIG. 2, the controller 150 may include, for example, an image acquisition part 151, a first control part 152, a first driving part 153, a second driving part 154, and a first communication part 155.

The image acquisition part 151 may acquire an image captured by a camera 410 provided inside the endoscope 400.

The image acquisition part 151 may be able to perform image processing on the acquired image.

The image may represent, for example, images of an affected area, a surrounding area of an affected area and/or at least one end effector. The image of the end effector 300 may include an image of a tip part 320 and a gauge display part 340.

The first control part 152 may control the operation of the arm 120 based on a command being transmitted from the console 200. The controlling of the arm may represent controlling an angle or a torque of at least one of the plurality of motors included in the arm.

The first control part 152 may control the operations of at least one camera 410 and a light 420 that may be provided inside the endoscope 400, and may control an angle of at least one motor 350 that me be provided inside the end effector 300 to perform a treatment or a surgery on an affected area. In addition, the first control part 152 may control the torque of the motor 350.

The first driving part 153 may drive the camera 410 and the light 420 that may be provided inside the endoscope 400 in response to a command by the first control part 152.

The camera 410 that may be provided inside the endoscope 400 may be provided in one unit thereof to capture a two dimensional (2D) image, or in two units thereof to capture a three dimensional (3D) image. The light 420 may include one or more lights. In addition, the camera 410 may be equipped with a zoom in/out function.

The endoscope 400, during a surgery, may turn on the light 420, and may drive the camera 410 to capture an image of the tip part and the gauge display part of the end effector 300.

The second driving part 154 may drive at least one motor 350 that may be included inside the end effector 300 such that the tip part 320 may operate in response to a command by the first control part 152.

The first communication part 155 may transmit an image to the console 200 according to a command by the first control part 152, and may receive driving commands for each motor being transmitted from the console 200 and may transmit the received driving command to the first control part 152. The motor represents a motor that may be included inside the plurality of arms and in the end effector.

The image represents an image of an affected area and at least one end effector, and the image of the end effector image 300 includes an image of a tip part and a gauge display part.

The first communication part 155 may transmit a torque and an angle data of each motor that may be included in the arm 120 to the console 200.

The console 200 may provide an operator with an image captured through the endoscope 400 of the manipulator 100, and may receive a surgical command from the operator to generate driving commands for the arm 120, the end effector 300, and the endoscope 400 in response to the surgical command being input, so that the arm 120, the end effector 300 and the endoscope 400 operate, thereby possibly performing a treatment and a surgery on the affected area.

The console 200 may include, for example, an input part 210, a second control part 220, a second communication part 230 and a second image panel 240.

The input part 210 may receive commands to control the arm 120 that may be included in the manipulator 100, the end effector 300, and the endoscope 400 from the operator.

The input part 210 may include, for example, at least one of a small size wrist gimbal, a joystick, a glove, a trigger-gun, and a speech recognition apparatus, etc.

The input part 210 may include a pedal configured to, for example, induce hemostat through cauterization, or to control the vertical movement of the arm 120.

The second control part 220 may generate driving commands for the arm 120, the end effector 300, and the endoscope 400 in response to the surgical command being input.

The second control part 220 may control transmitting of the driving command for the motor that may be included inside the arm 120, the driving command for the end effector 300 and the driving command for the endoscope 400.

The second control part 220 may control storing of the angle or the torque of a plurality of motors included in the arm 120 and a plurality of motors included in the end effector 300.

The second control part 220 may control outputting of the image being transmitted from the manipulator 100.

The second control part 220 may control displaying of the image according to a command by the operator being input through the input part 210, so that an enlarged view of the gage display part of the end effector 300 may be displayed.

The second communication part 230 may perform a wired/wireless communication with the first communication part 155 of the manipulator 100.

The second communication part 230 may transmit signals to control the arm 120 that may be included in the manipulator 100, the end effector 300 and the endoscope 400, and may receive an image signal from the manipulator 100.

In addition, the second communication part 230 may receive an angle or a torque of the motor that may be included in the arm 120 of the manipulator and in the end effector 300.

The second image panel 240 may display a surgery image. Hereinafter, the displaying of the surgery image will be described with reference to FIGS. 3A and 3B.

Figure 3A:
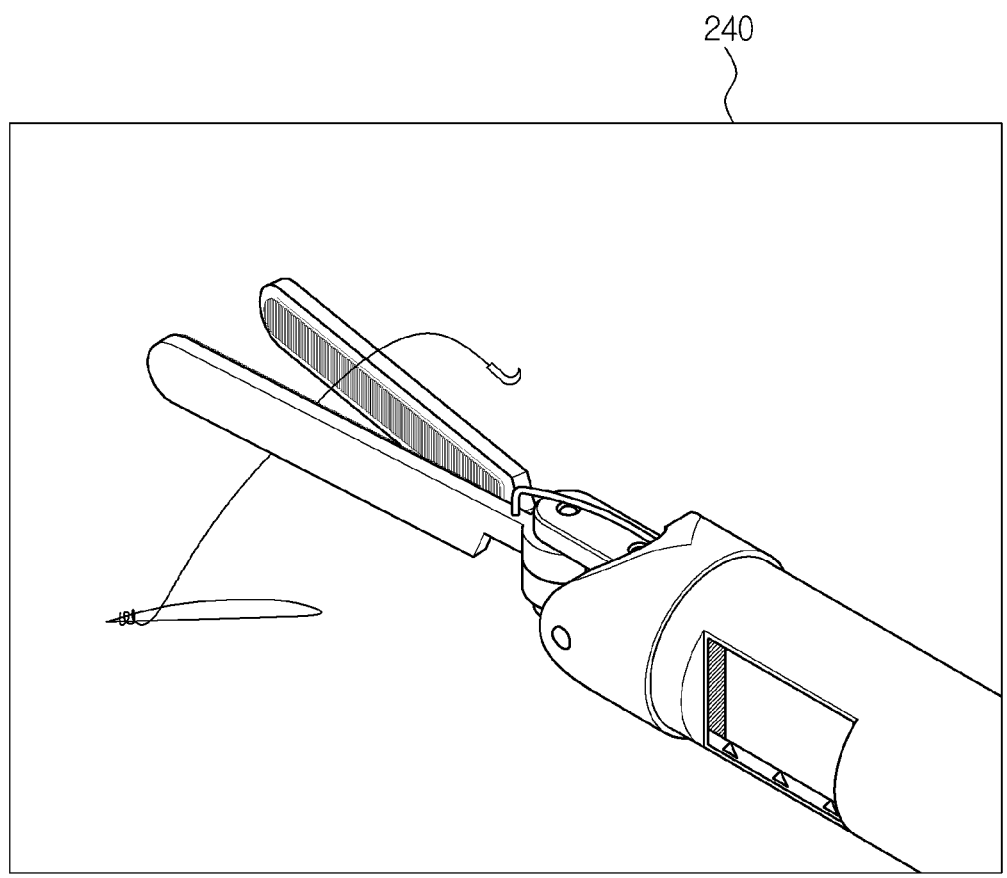
FIGS. 3A and 3B are views showing an example of enlarging an image through a console of a remote control apparatus in accordance with one or more embodiments, such as the remote control apparatus of FIG. 1.

Referring to FIG. 3A, the second image panel 240 may display an image being transmitted from the manipulator 100, thereby possibly providing the operator with a surgery image.

The image may include, for example, images of an affected area, a surrounding area of an affected area and at least one end effector 300. The image of the end effector 300 may include, for example, an image of the tip part 320 and the gauge display part 340.

Figure 3B:
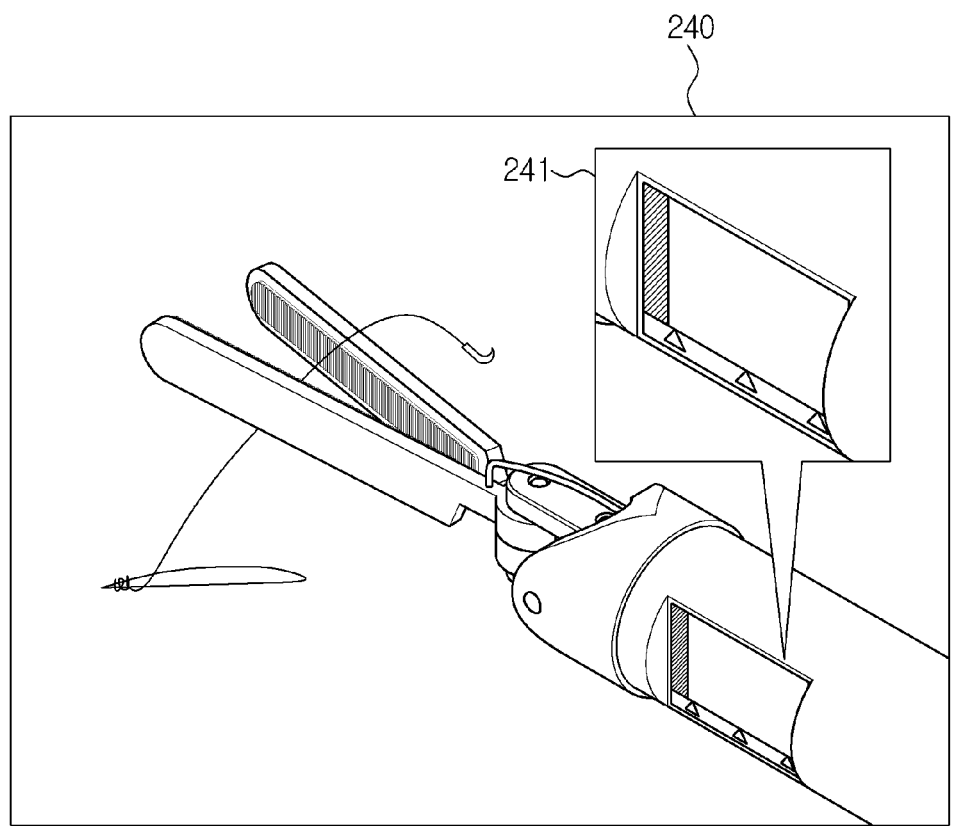

Referring to FIG. 3B, the second image panel 240 may display an enlarged image 241 of the gauge display part at a periphery of the image of the end effector according to a command by the second control part 220.

Accordingly, the operator may check the gauge of physical information about an object according to contact with an object.

The second image panel 240 may convert the image being transmitted from the manipulator 100 into a stereo image and may display the converted image in real time such that the operator may manipulate the arm, the end effector and the endoscope while observing the affected area.

The console 200 may include a stereo lens configured such that an image being displayed through the second image panel may be viewed in a dimensional image.

Figure 4:
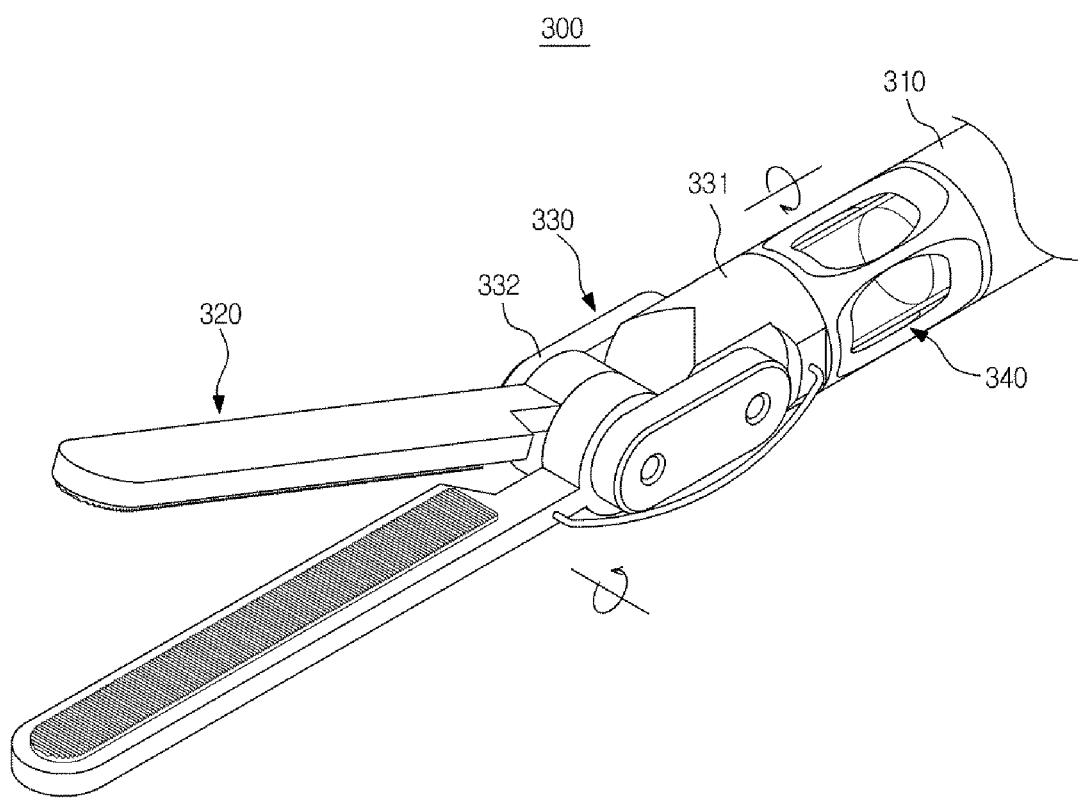
FIG. 4 is a perspective view of a gauge display part of an end effector in accordance with one or more embodiments.
Figure 5A:
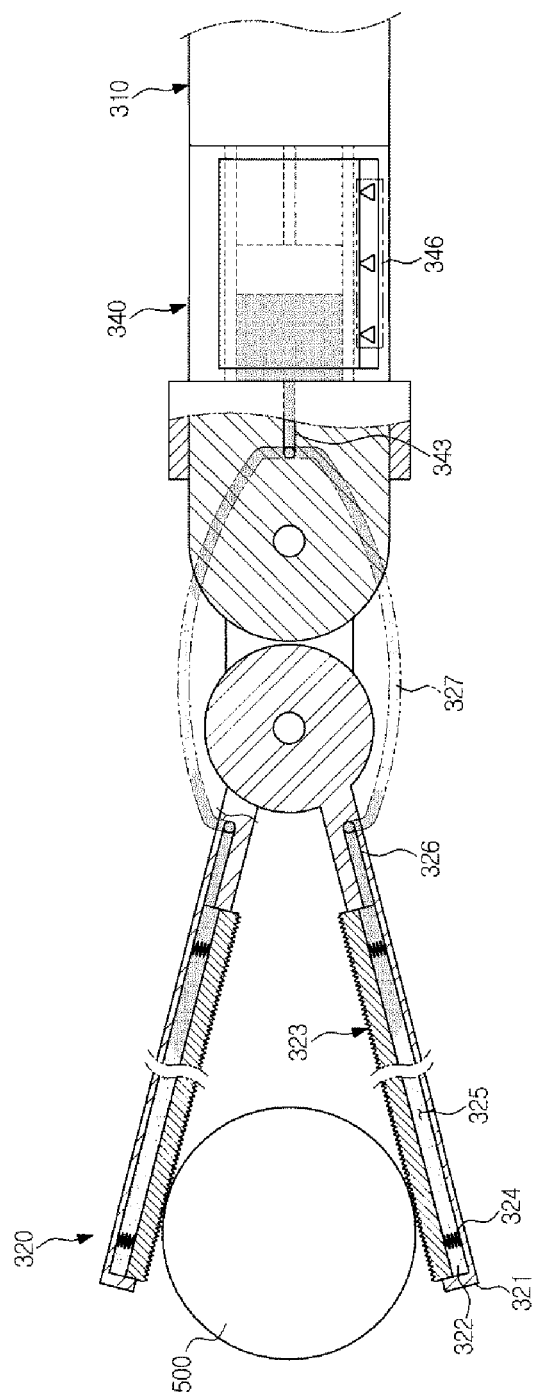
FIGS. 5A and 5B are cross sectional views illustrating an end effector in accordance with one or more embodiments, such as the end effector of FIG. 4.
Figure 5B:
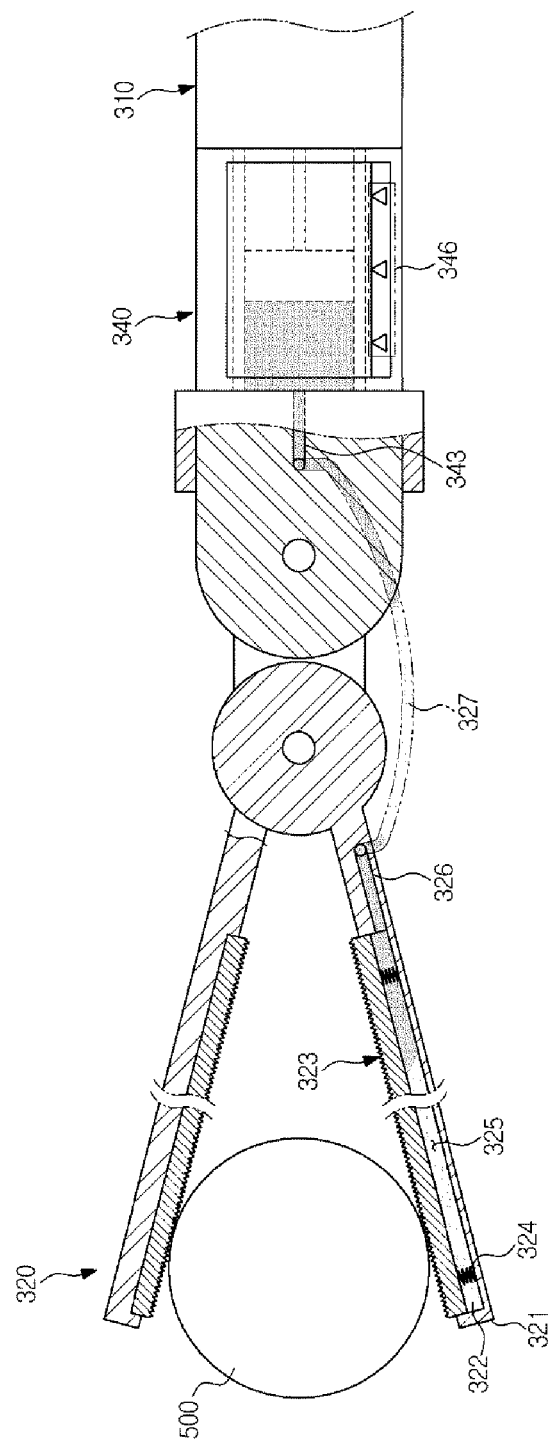

FIG. 4 is a perspective view of a gauge display part of an end effector in accordance with one or more embodiments. FIG. 5 is a perspective view of an end effector in accordance with one or more embodiments. FIGS. 5A and 5B are a cross sectional view of an end effector in accordance with one or more embodiments, such as the end effector of FIG. 4. Hereinafter, the end effector will be described with reference to FIGS. 4 and 5 in conjunction with FIGS. 6 to 9.

Referring to FIGS. 4 and 5A and 5B, the end effector 300 may include, for example, a connecting rod part 310, the tip part 320, a joint part 330, and the gauge display part 340.

The connecting rod part 310 may be mechanically fastened to the arm 120 so as to be detached from the arm 120, and may be electrically connected to the arm 120 to receive a driving command for the joint part 330 through the arm 120 and transmit the transmitted driving command to the joint part 330.

The tip part 320 may directly perform a treatment and a surgery. The tip part 320 may include, for example, one of scissors, a gripper, a needle holder, a micro-dissector, a staple applier, a tacker, a suction irrigation tool, a clip applier, a cutting blade, an irrigator, a catheter, and a suction orifice, etc.

In addition, the tip part 320 may include, for example, one of an electric surgical probe for ablating, an electric surgical probe for resecting, an electric surgical probe for cutting, and an electric surgical probe for coagulating of a tissue, etc.

The following description will be made in relation to the tip part 320 formed using a gripper as an example, in which the tip part 320 is provided in one pair so as to enable grapping of an object.

Referring to FIG. 5A, the one pair of tip parts may be each provided in the same structure to detect a force applied to an object. Referring to FIG. 5B, the one pair of tip parts may be each provided in the different structure so that one tip part is used to detect a force applied to an object and the remaining tip part is used to perform a gripping.

Hereinafter, the structure of the tip part 320 to detect the magnitude of force, corresponding to physical information according to contact with an object will be described.

Figure 6:
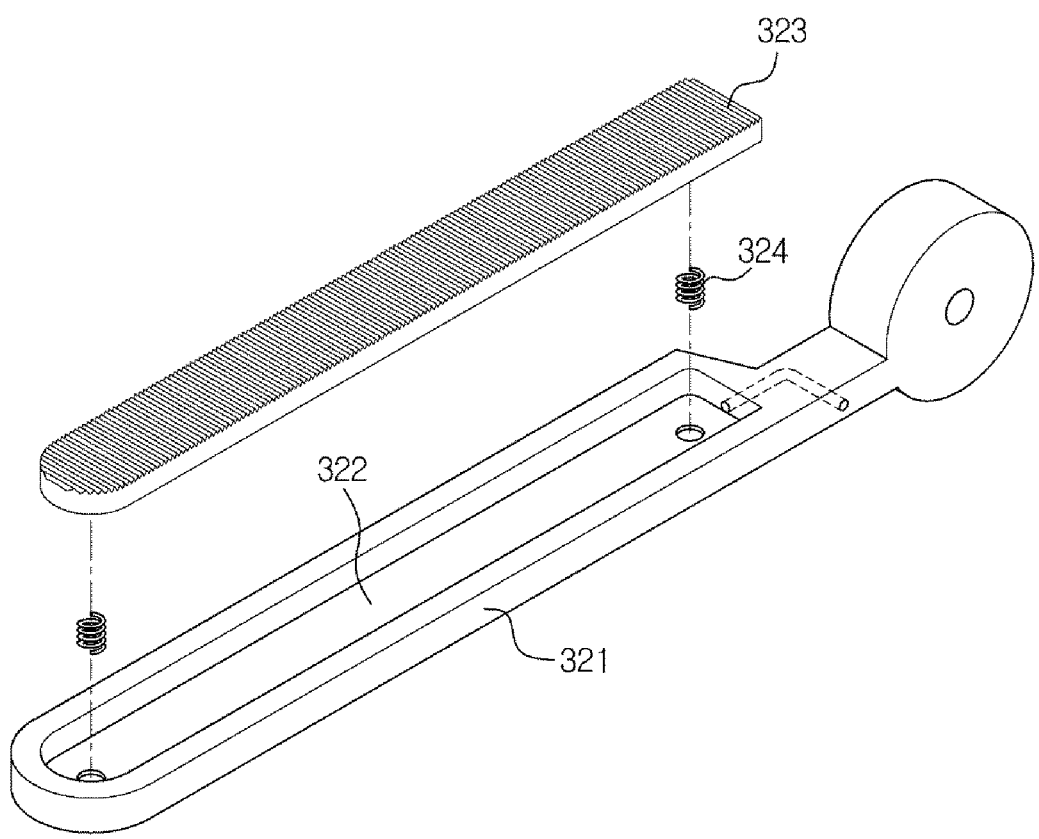
FIG. 6 is an exploded perspective view illustrating a tip part of an end effector in accordance with one or more embodiments, such as the end effector of FIG. 4.

Referring to FIG. 6, the tip part 320 includes, for example, a body 321, a deformation part 322, a contact member 323, an elastic member 324 and a fluid 325.

The body 321 may form the external appearance of the tip part 320. The body 321 may include a connection member connected to the joint part 330.

The deformation member 322 may be accommodated inside the body 320, and may change the physical information thereof according to contact with an object at the time of contact with an object. The changed physical information may be transmitted to the gauge display part 340.

The physical information may be, for example, one information among the temperature and the humidity of an object, the illuminance of a surrounding environment and the force applied to an object, etc.

If the physical information is a force applied to an object, the deformation member 322 may change the external appearance thereof according to the force applied to the object at the time of contact with the object.

Since the fluid 325 is filled in the deformation member 322, as the deformation member 322 may be pressed by the force applied to the object, the fluid filled in the deformation member 322 may move to the outside. The fluid 325 may include gas or liquid that is movable.

The contact member 323 may be a member making a direct contact with an object. The contact member 323 may be mounted at the body 321 so as to be movable to the inside the body 321.

The contact member 323 may press the deformation member 322 while moving to the inside the body 321 due to the force applied to the object.

A friction part may be formed on a surface of the contact member 323. The friction part may improve the gripping performance by enhancing the frictional force with the object.

The elastic member 324 may be located between the body 321 and the contact member 323. When the gripping force with respect to the object is decreased from a state of the contact member 323 being moved to the inside the body 321, the elastic member 324 may provide the contact member 323 with a restoring force.

At the same time of the contact member 323 being restored, the fluid moved to the outside may be filled in the deformation member 322 again.

The elastic member 324 may include, for example, at least one spring.

The end effector may further include a first connection pipe 326 and a second connection pipe 327 that may be configured to deliver the fluid 325 between the deformation member 332 of the tip part 332 and the gauge display part 340.

The first connection pipe 326 may be connected to the deformation member 332, and the second connection pipe 327 may be disposed between a third connection pipe 343 connected to the gauge display part 340 and the first connection pipe 326 so as to connect the third connection pipe 343 to the first connection pipe 326.

The first connection pipe 326 may be integrally formed with the second connection pipe 327.

The first connection pipe 326, the second connection pipe 327 and the third connection pipe 343 may be integrally formed with one another.

The joint part 330 may include at least one motor 350 to move the tip part 320 according to the driving of the motor 350, so that the object may be gripped between the one pair of tip parts 320.

The joint part 330 may include a first joint 331 that may be formed in an extension direction of the connecting rod part 310 to rotate on a straight axis parallel to the extension direction of the connecting rod part 310, and a second joint 332 that may be connected between the first joint 331 and the tip part 320 to rotate on an axis perpendicular to the extension direction.

Each of the first joint 331 and the second joint 332 may include the motor 350, thereby possibly enabling the tip part 320 to perform a multi axes direction operation according to the driving of the motor 350.

The motor 350 that may be included in the first joint 331 and in the second joint 332 may be electrically connected to the connecting rod part 310 through a cable (not shown). That is, the cable may transmit electric signals, being transmitted through the arm 120, to the motor 350.

Although the above description has been made in relation to the end effector having two joints and two motors, the present disclosure is not limited thereto. For example, the end effector may include one joint and one motor, or include more than three joints and more than three motors.

The gauge display part 340 may display the amount of the fluid 325 being transmitted from the deformation member 332 through the first, second and third connection pipes 326, 327 and 343. The amount of fluid may correspond to the force applied to the object, that is, the physical information according to contact with the object.

In detail, when an object is gripped by use of the one pair of tip part 320, a repulsive force to the gripping force may be generated at the object. Due to the repulsive force, a movement pressure maybe generated at the contact member 323 of the tip part 320, and the deformation member 322 may be pressed by the movement pressure exerted on the contact member 323.

In this case, the fluid 325 inside the deformation member 322 may receive pressure by Pascal's law, and may move to the gauge display part 340 through the first, second and third connection pipes 326, 327 and 343 and then may generate pressure at the gauge display part 340.

That is, as the pressure at the contact member of the tip part is increased, the amount of fluid inside the gauge display part may be increased, and thus the force applied to the object may be recognized based on the distance moved by a piston corresponding to the increased amount of fluid. The relationship between the force applied to the object and the moving distance of the piston may be explained through the following equation.

$$Pt/At = Pg/Ag, \; AtLt = AgLg$$

Herein, Pt represents the pressure applied to the contact member, At represents an area at which the contact member makes contact with the deformation member, Pg represents a pressure induced at the cylinder of the gauge display part, Ag represents an area of the cylinder of the gauge display part, Lt is a movement displacement of the contact member, and Lg is a movement displacement of fluid inside the cylinder of the gauge display part, that is, the movement displacement of the piston.

The gauge display part 340 may include the cylinder 341 and the piston 342. Hereinafter, the gauge display part 340 will be described with reference to FIG. 7.

Figure 7:
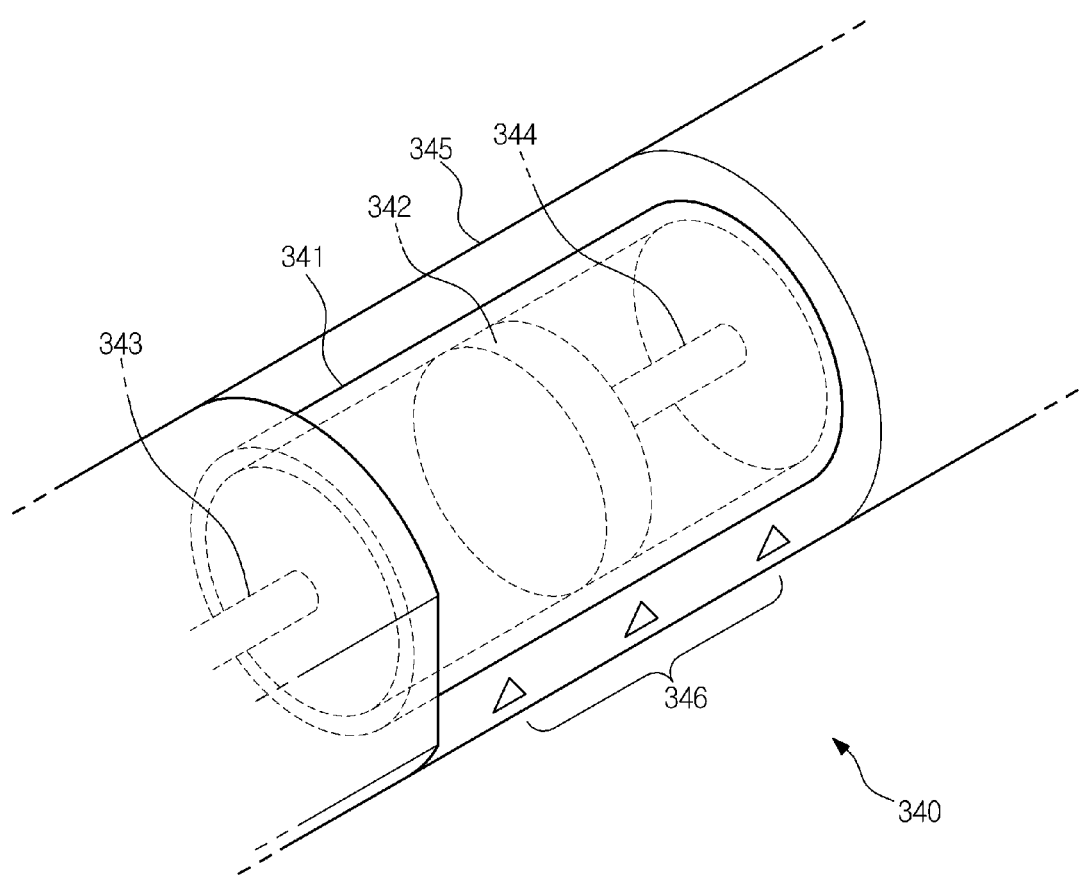
FIG. 7 is a perspective view of a gauge display part of an end effector in accordance with one or more embodiments, such as the end effector of FIG. 4.

Referring to FIG. 7, the cylinder 341 may be a cylindrical container allowing the fluid inside the deformation member 332 to be admitted and discharged into or from the deformation member according to the gripping of the object and the magnitude of the gripping force.

A hole may be formed through the cylinder 341, and the third connection pipe 343 may be connected to the hole so that the fluid may be admitted or discharged through the third connection pipe 343.

The cylinder 341 may be formed of transparent material enabling the position of the piston 342 inside the cylinder 341 to be identified.

The fluid may be formed of a color fluid so that the movement of the fluid inside the cylinder 341 may be identified.

The piston 342 may be disposed while coming into close contact with the inside the cylinder 341, and may reciprocate inside the cylinder 341 according to the pressure generated by the fluid admitted or discharged from/into the deformation member 332 through the third connection pipe 343.

That is, the magnitude of the force applied to the object gripped by the tip part 320 may be detected from the position of the piston 332 reciprocating according to the pressure of the fluid admitted or discharged from/into the deformation member 332.

The gauge display part 340 may further include a restoring member 344 to provide the piston 342 with a restoring force.

That is, when the object is released or the force gripping the object is decreased, the restoring member 344 may provide the piston 342 with a restoring force so that the piston 342 returns to the original position. Due to the restoring force of the piston 342, the fluid 325 inside the cylinder 341 may be transmitted to the deformation member 322.

The gauge display part 340 may further include a housing 345 to protect the cylinder 341.

The housing 345 may also be formed of transparent material enabling the position of the piston 342 inside the cylinder 341 to be identified.

In addition, a part of the housing 345 may be formed of transparent material, and the remaining part of the housing 345 may be formed of non-transparent material. Through the transparent part, the magnitude of a force corresponding to the position of the piston 342 may be identified.

The gauge display part 340 may further at least one scale 346 that may indicate the magnitude of a force so that the magnitude of force applied to the object may be identified.

The scale 346 may be formed, for example, at a boundary among a safety area, a warning area and a caution area.

The operator may check the scale formed at a position corresponding to the position of the piston 342, thereby possibly recognizing the magnitude of the force applied to the object.

In addition, the cylinder 341 may be provided with semi-transparent coating layers coated thereon, each having a different color to indicate the magnitude of a force.

For example, a green coating layer indicating a safety range, an orange coating layer indicating a warning range, and a red coating layer indicating a caution range may be coated on the surface of the cylinder 341. The piston 342 may be formed of non-transparent material.

Accordingly, the position of the piston 342 of non-transparent material may be represented through the semi-transparent cylinder.

That is, the operator may recognize the magnitude of the force applied to the object by checking the color of the coating layer corresponding to the position of the piston 342.

The gauge display part 340 may be disposed, for example, at the connecting rod part 310, in detail, at a portion of the connecting rod part 310 adjacent to the tip part 320.

Accordingly, the gauge display part 340 may be disposed within a field of view (FOV) of the camera 410 inside the endoscope 400.

As described above, the gauge display part 340 may be disposed at a surrounding area of the tip part 320 of the end effector, so that the physical information about the object exerted on the tip part of the end effector may be collected in the form of an image.

In addition, the whole of the cylinder 341 of the gauge display part 340 may be formed to be transparent, so that the position of the piston 342 inside the cylinder 341 may be checked from various angles.

That is, the image of the gauge display part 340 of the end effector may be collected at various angles when collecting images through the endoscope 400.

The physical information related to force applied to the object may be obtained in the form of an image, the image about the physical information such as force may be transmitted to the console 200, and the image may be displayed through the second image panel of the console 200, thereby enabling the operator to indirectly feel the force or the tactile sensation generated at the end effector.

Figure 8A:
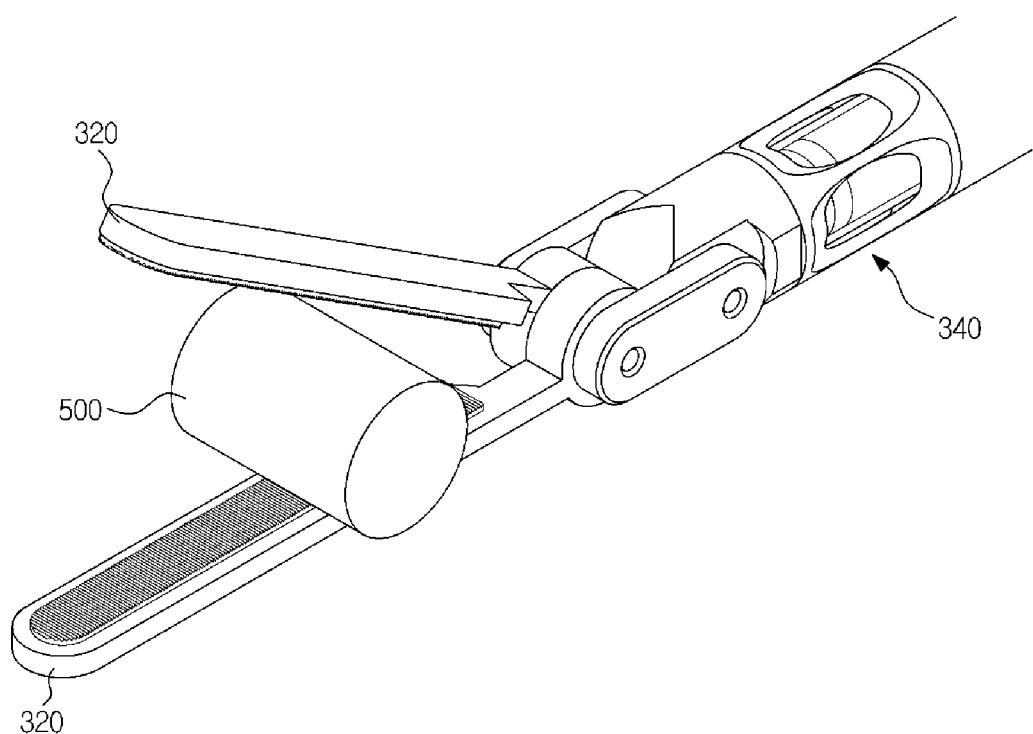
FIGS. 8A to 8C are exemplary views illustrating a gauge display of the gauge display part of an end effector in accordance with one or more embodiments, such as the end effector of FIG. 4.
Figure 8B:
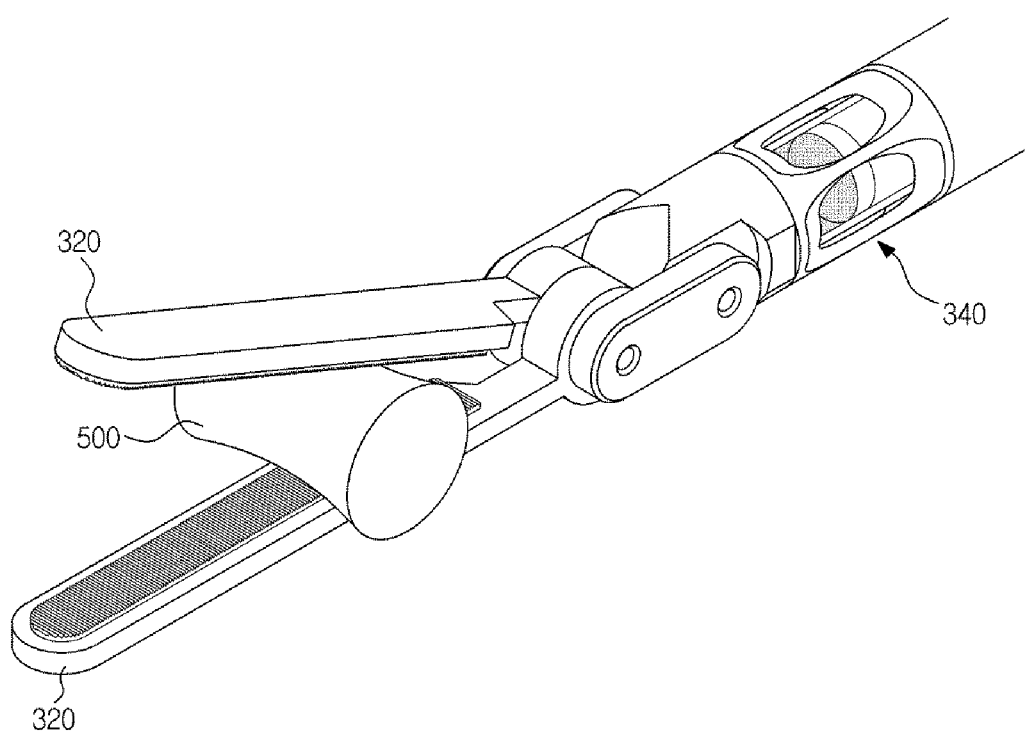
Figure 8C:
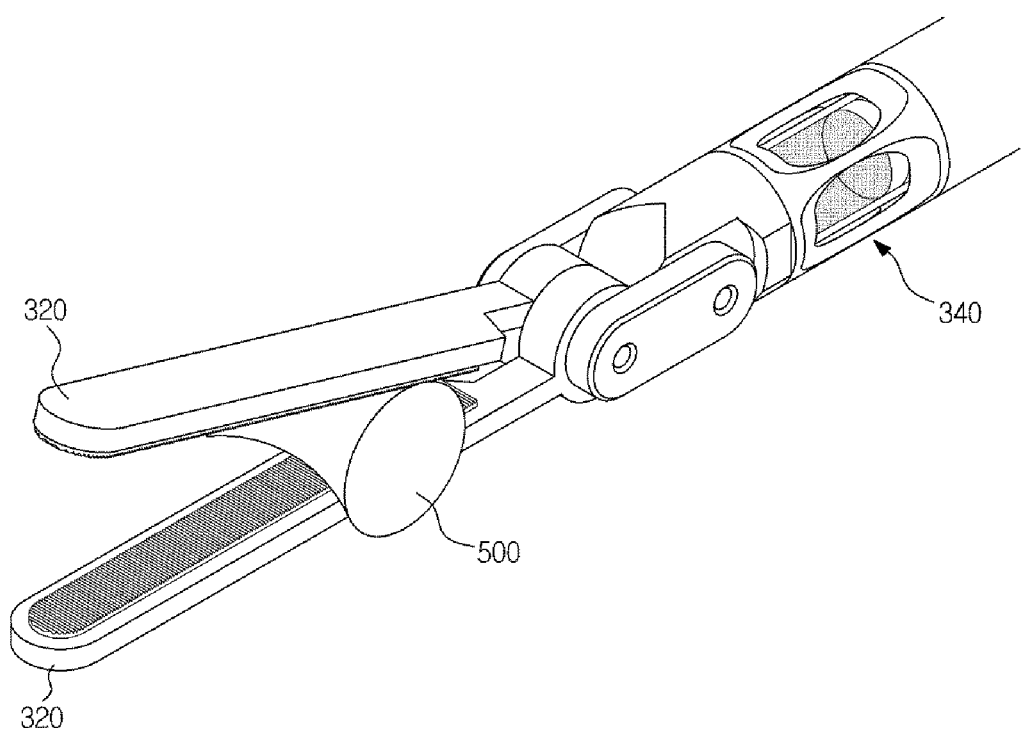

FIGS. 8A to 8C are exemplary views of the gauge display of the gauge display part of an end effector in accordance with one or more embodiments, such as the end effector mounted at the manipulator of the remote control apparatus, illustrating the position of the piston 342 according to the movement of the fluid corresponding to the force applied to the object 500.

Referring to FIG. 8A, the piston 342 may be located at an initial position before the object 500 is gripped by the one pair of tip parts 320.

At this time, a force may not be applied to the object 500 from the one pair of tip parts 320, so the fluid 325 may not be transmitted from the deformation member 332 to the cylinder 341. That is, a movement of the piston 342 inside the cylinder 341 may not occur, and thus the piston 342 may be located at the initial position.

Referring to FIG. 8B, the object 500 may be gripped by the one pair of tip parts 320 and an appropriate force may be applied to the object 500, and thus the piston 342 may be located at a safety area.

At this time, the appropriate force may be applied to the object 500 from the one pair of tip part 320, and the amount of fluid 325 corresponding to the applied force may be transmitted from the deformation member 332 to the cylinder 341. That is, the piston 342 may be located at a safety area according to the pressure being transmitted from an appropriate amount of fluid 325.

Referring to FIG. 8C, the object 500 may be gripped through the one pair of tip parts 320 and an excessive force may be applied to the object 500. The piston 342 may be located at a caution area.

At this time, the excessive force may be applied to the object 500 from the one pair of tip part 320, and a large amount of fluid corresponding to the applied force may be transmitted from the deformation member 332 to the cylinder 341. Accordingly, the piston 342 may be located at a caution area according to the pressure transmitted from the large amount of fluid.

Figure 9:
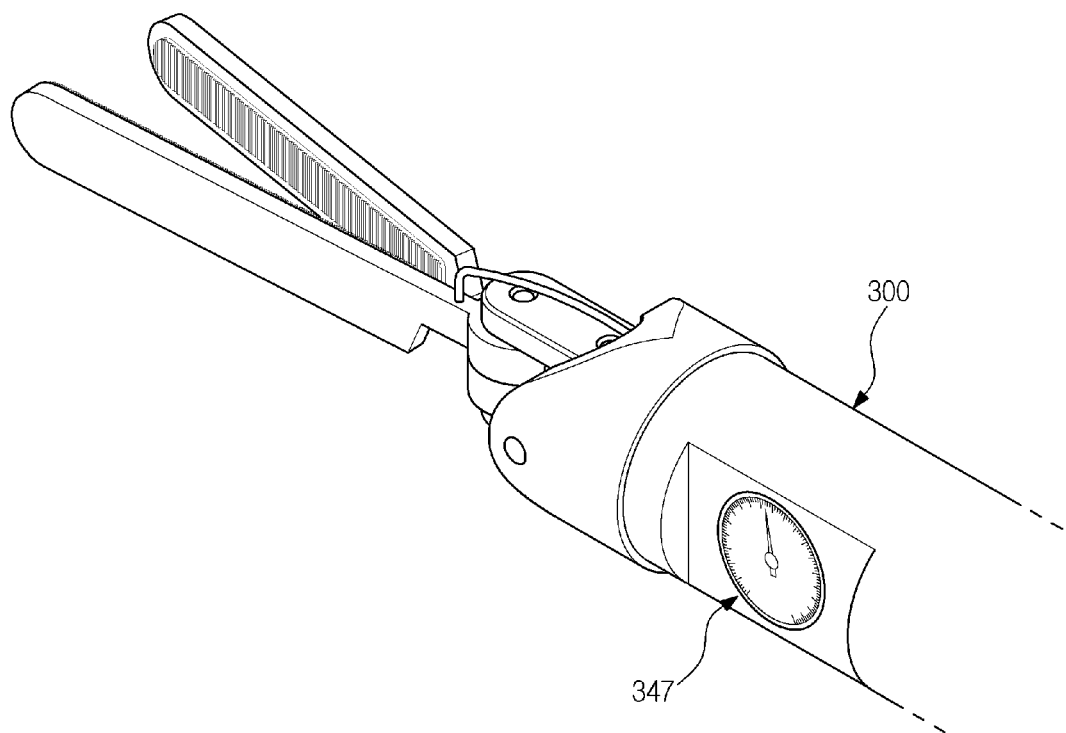
FIG. 9 is an exemplary view illustrating a gauge display part of an end effector in accordance with one or more embodiments.

FIG. 9 is an exemplary view illustrating a gauge display part of an end effector in accordance with one or more embodiments.

Referring to FIG. 9, the gauge display part of the end effector may further include a dial gauge 347.

The dial gauge 347 may rotate a pointer on a scale plate by increasing the movement of a spindle (not shown), which may be connected to the piston 342 of the gauge display part 340, for example, by use of a gear.

The spindle may include a rack, and may transmit the movement of the rack to the gear.

The pointer of the dial gauge 347 may rotate based on the distance between an original position and a moved position of the piston 342.

The piston 342 may further include an interlocking member (not shown) that may interact in conjunction with the reciprocation of the piston 342, and the interlocking member may be connected to the spindle.

Figure 10:
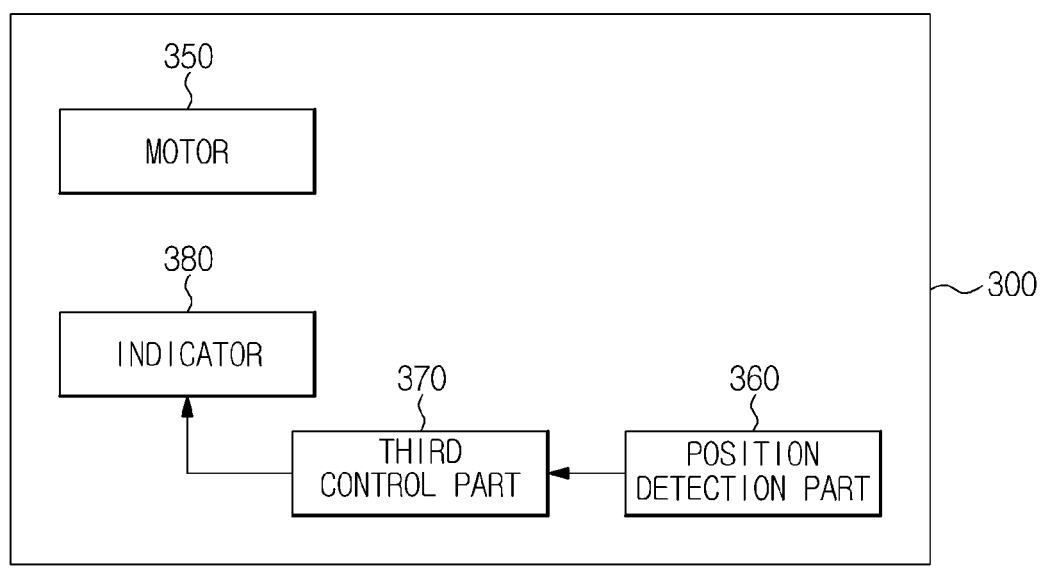
FIG. 10 is a control block diagram of an end effector in accordance with one or more embodiments.

FIG. 10 is a control block diagram of an end effector in accordance one or more embodiments. The end effector 300 may include, for example, a position detection part 360, a third control part 370, and an indicator 380.

The motor 350 may be located at the joint part 330 as the above described one or more embodiments, and may operate by receiving a driving command through the connecting rod 310, so that the tip part 320 may operate.

The position detection part 360 may detect the position of the piston 342.

The third control part 370 may generate an electric signal corresponding to the position of the piston 342 that may be detected through the position detection part 360, and may allow gauge information corresponding to the generated electric signal to be displayed in an electric manner.

The indicator 380 may display gauge information corresponding to an electric signal in an electric manner according to a command of the third control part 370.

Hereinafter, examples of the indicator 380 will be described with reference to FIGS. 11 to 14.

Figure 11:
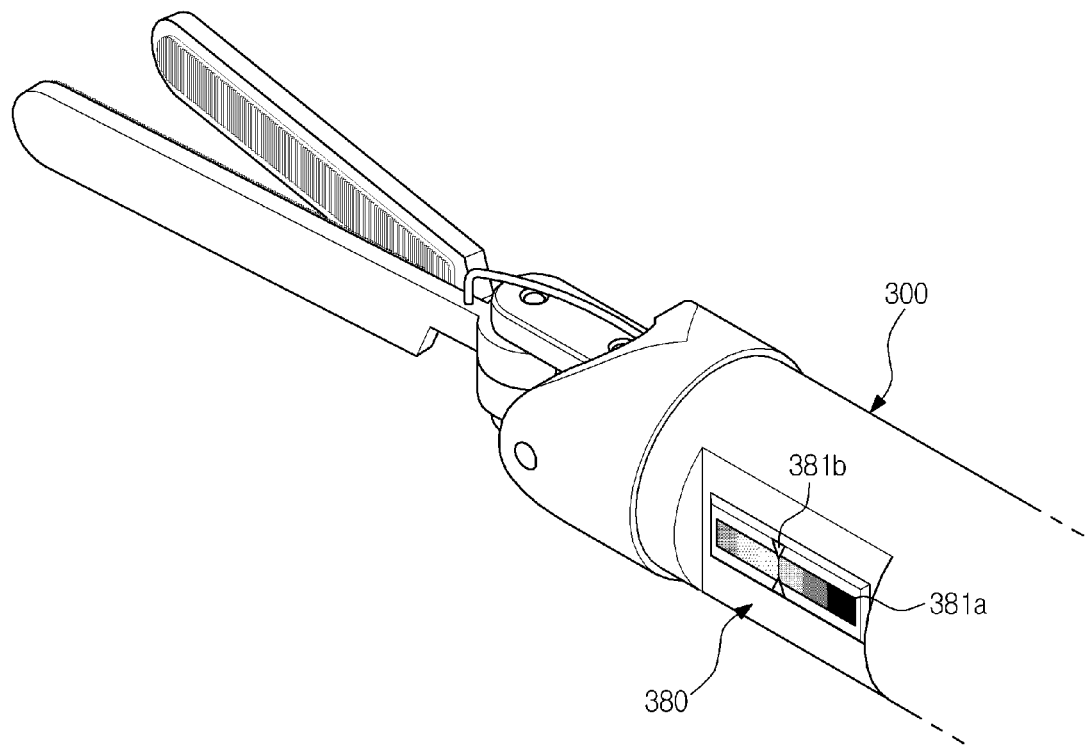
FIG. 11 is a view of an example of an indicator included in an end effector in accordance with one or more embodiments, such as the end effector of FIG. 10.

Referring to FIG. 11, the indicator 380 may include a color panel 381a configured to display a safety level and a caution level through different colors in a varied degree of brightness, and an indication bar 381b configured to move according to a command by the third control part 370 while being installed adjacent to the color panel 381a.

In detail, for example, a safety range of the color panel 381a may have green bands consecutively disposed in a varied degree of brightness according to a safety level, and a caution range of the color panel 381a may have red bands consecutively disposed in a varied degree of brightness according to a caution level. In addition, instead of the brightness, the saturation may be varied according to the safety level and the caution level.

The indication bar 381b may move to a position of a color bar corresponding to the magnitude of force applied to the object.

In this case, the third control part 370 may determine a magnitude of a force corresponding to the position of the piston, may determine a position of a color band corresponding to the determined magnitude of the force, and may control the driving of the indication bar 381b such that the indication bar 381b may move to the determined position.

The bar gauge may be implemented, for example, using a vertical bar gauge or a horizontal bar gauge.

Figure 12A:
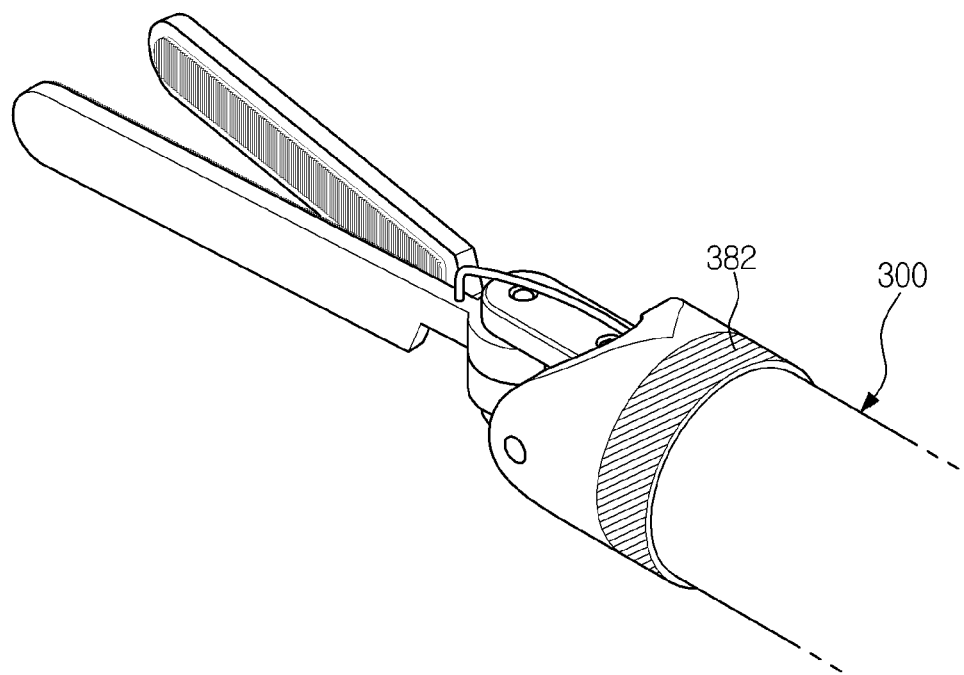
FIGS. 12A and 12B are views of an example of an indicator included in an end effector in accordance with one or more embodiments, such as the end effector of FIG. 10.
Figure 12B:
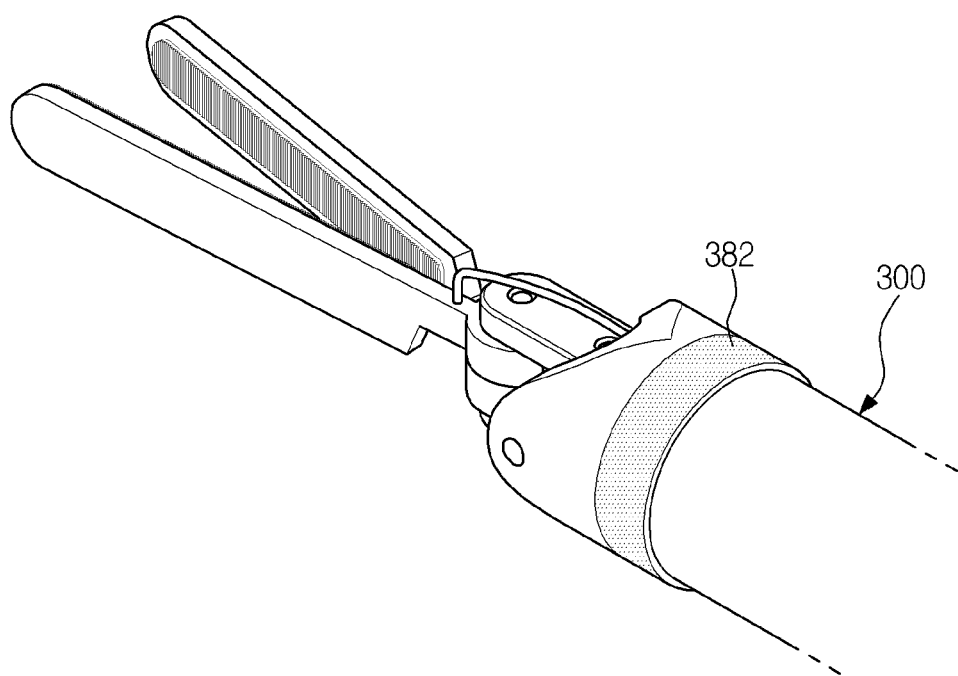

Referring to FIGS. 12A and 12B, the indicator 380 may include an RGB LED 382 to display colors corresponding to a safety range, a warning range and a caution rage.

That is, the RGB LED 382 may adjust the lighting and the brightness level of a red light emitting diode (R), a green light emitting diode (G), and a blue light emitting diode (B) so as to display a color corresponding to a command by the third control part 370.

Accordingly, referring to FIGS. 12A and 12B, the RGB LED 382 may light in a different color according to the magnitude of the force applied to the object.

In this case, the third control part 370 may determine a magnitude of a force corresponding to the piston, may check a color corresponding to the determined magnitude of the force, may generate a driving command for the red light emitting diode (R), the green light emitting diode (G), and the blue light emitting diode (B) and may transmit the generated driving command to the RGB LED 382.

Figure 13:
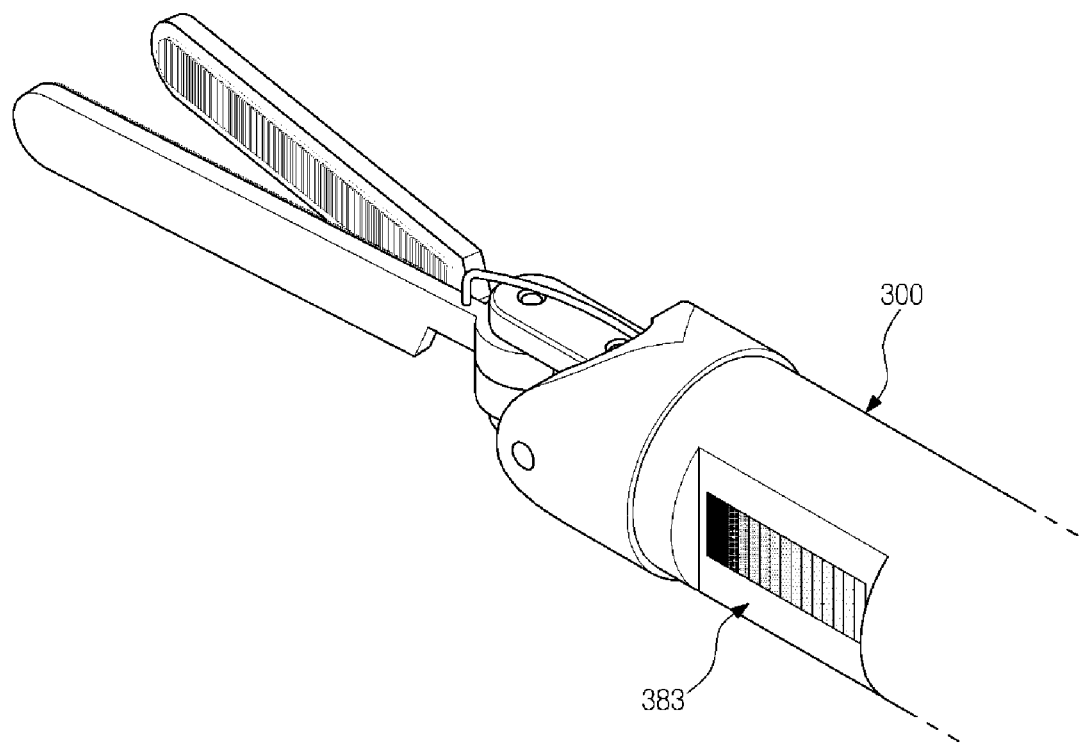
FIG. 13 is an exemplary view of an indicator included in an end effector in accordance with one or more embodiments, such as the end effector of FIG. 10.

Referring to FIG. 13, the indicator 380 may include a plurality of light emitting diodes 383 to turn on colors corresponding to a safety range, a warning range and a caution range.

That is, the plurality of light emitting diodes 383 may turn on at least one of the plurality of light emitting diodes according to a command by the third control part 370.

In this case, the third control part 370 may determine a magnitude of a force corresponding to the position of a piston, may check a light emitting diode having a color corresponding to the determined magnitude of force, and may control a lighting of the plurality of light emitting diodes such that a light emitting diode having the corresponding color is turned on.

Figure 14:
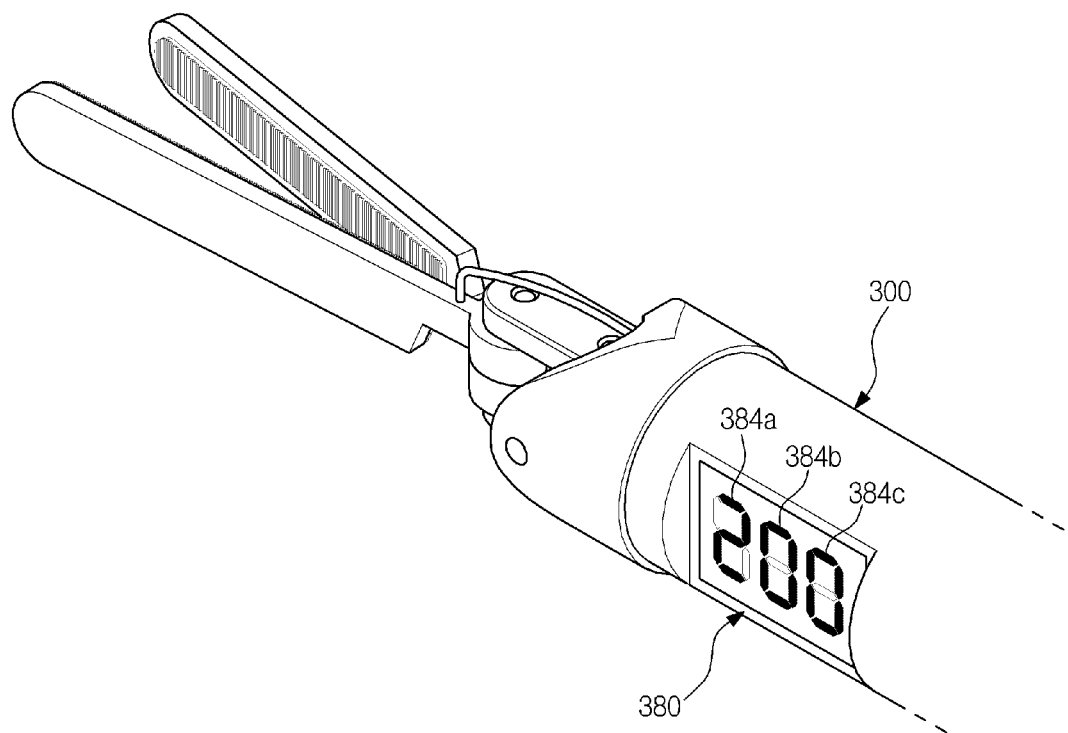
FIG. 14 is an exemplary view of an indicator included in an end effector in accordance with one or more embodiments, such as the end effector of FIG. 10.

Referring to FIG. 14, the indicator 380 may include at least one unit of a seven segment display to display a numeric value corresponding to the magnitude of the force applied to the object.

In FIG. 14, three units of seven segment display 384a, 384b and 384c are illustrated.

The three units of seven segment display 384a, 384b, and 384c may represent a numeric value ranging from 0 to 9 by turning on at least one light emitting diode according to a command by the third control part 370. The numeric value displayed through three units of the seven segment display may correspond to a magnitude of force applied to the object.

In this case, the third control part 370 may determine a magnitude of a force corresponding to the position of the piston, may check a numeric value corresponding to the determined magnitude of the force, may determine a light emitting diode in each unit of seven segment display that is to be turned on, and may transmit a driving command for the determined light emitting diode to the three units of the seven segment display 384a, 384b, and 384c.

Figure 15:
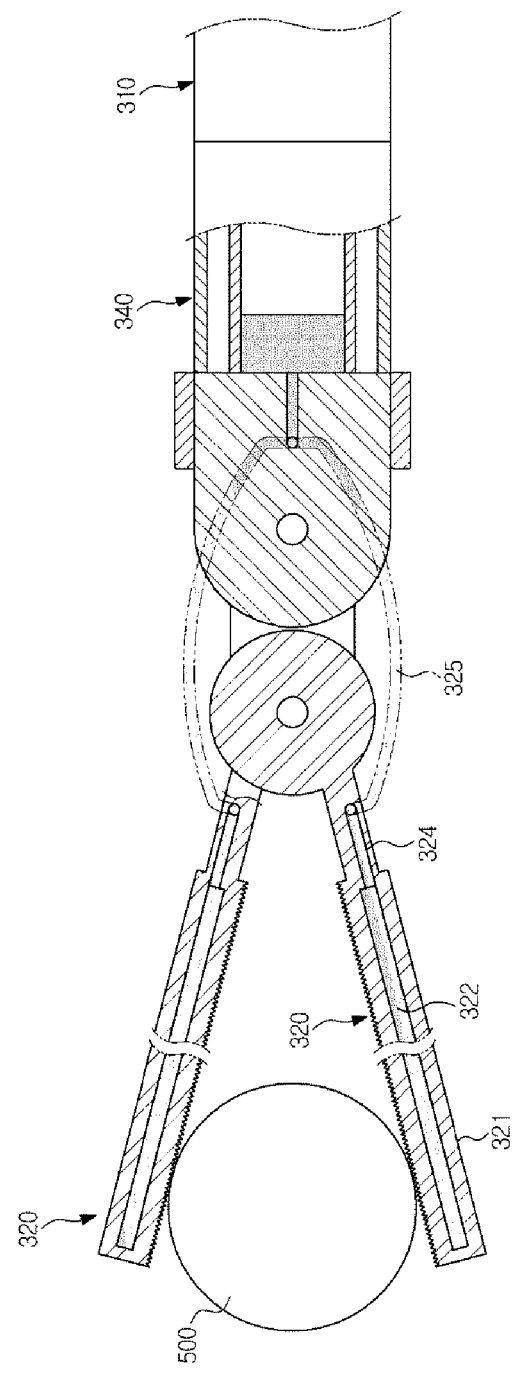
FIG. 15 is an exemplary view of an end effector in accordance with one or more embodiments.

FIG. 15 is an exemplary view of an end effector in accordance with one or more embodiments. The end effector may include, for example, the connecting rod part 310, the tip part 320, the joint part 330, and the gauge display part 340.

The connecting rod part 310 and the joint part 330 in accordance with this embodiment are identical to those in the above described embodiment of the present disclosure as shown in FIG. 4, and thus detailed description thereof will be omitted.

The tip part 320 may detect the temperature or humidity, that is, the physical information according to contact with the object. Hereinafter, the structure of the tip part 320 will be described.

Referring to FIG. 15, the tip part 320 may include, for example, a body 321 that may form the external appearance of the tip part 320, a deformation member 322 that may be accommodated inside the body 320 and in which a fluid having physical information thereof varied according to contact with an object at the time of contact with an object may be filled, a contact member 323 configured to make contact with an object and transmit physical information about the object to the deformation member 322, and a fluid. The contact member may be optionally omitted.

The physical information may represent, for example, the temperature or humidity of an object, and the fluid may be a liquid or a gas that changes a color thereof according to the temperature or humidity. In addition, the fluid may be a liquid or a gas that changes a volume thereof according to the temperature or humidity.

The physical information may be illuminance at a surrounding environment. That is, by using a fluid that changes a color thereof according to the illuminance of a surrounding environment, the illuminance of the surrounding environment may be detected and the detected illuminance may be directly displayed through the end effector.

The end effector may further include the first connection pipe 326 and the second connection pipe 327 that may be configured to transmit a fluid between the deformation member 322 of the tip part 320 and the gauge display part 340.

That is, in a case that the fluid is a liquid or a gas that changes a color thereof according to the temperature or humidity, the fluid may be made to move through the first, second and third connection pipes according the temperature or humidity such that the color of fluid accommodated in the gauge display part 340 may be changed.

In addition, in a case that the fluid is a liquid or a gas that changes a volume thereof according to the temperature or humidity, the piston may be made to reciprocate in conjunction with the change in volume according to the temperature or humidity, such that physical information according to the temperature or humidity may be displayed on the gauge display part 340.

As is apparent from the above, the accuracy of detection of physical information according to contact with an object may be enhanced. That is, when an outside master part obtains physical information about an object, a process of converting detected physical information into electric signals may be omitted, thereby inhibiting the influence of noise.

Accordingly, an operator may perform, for example, a surgery.

In addition, since physical information may be transmitted together with an image of an end effector between a robot and a console of a remote control apparatus, a process of transmitting an electric signal accompanied by detection of the physical information may be omitted between the robot and the console of the remote control apparatus, so the data flow between the robot and the console may be simplified and the network traffic may be reduced.

In addition, since the end effector and physical information about an object exerted on the end effector may be simultaneously displayed in an image, an additional program and algorithm operation for an augmented reality (AR) may be omitted, and thus the operating cost may be reduced while possibly improving the maintenance quality.

In addition, since an image including the physical information about an object may be displayed at an end effector, a process for synchronizing a time of display an image of the end effector with a time of displaying an image of physical information may be omitted. Accordingly, a program between a console and a robot of a remote control apparatus may be simplified.

In addition, a remote control may be performed in consideration of force and tactile sensation without installing a high-priced haptic device at a console for the feedback of the movement sensation and the tactile sensation.

In one or more embodiments, any apparatus, system, element, or interpretable unit descriptions herein include one or more hardware devices or hardware processing elements. For example, in one or more embodiments, any described apparatus, system, element, retriever, pre or post-processing elements, tracker, detector, encoder, decoder, etc., may further include one or more memories and/or processing elements, and any hardware input/output transmission devices, or represent operating portions/aspects of one or more respective processing elements or devices. Further, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include: magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be any defined, measurable, and tangible distributed network, so that the computer readable code is stored and executed in a distributed fashion. Still further, as only an example, the processing element could include a processor or a computer processor, and processing elements may be distributed and/or included in a single device.

The computer-readable media may also be embodied in at least one application specific integrated circuit (ASIC) or Field Programmable Gate Array (FPGA), as only examples, which execute (e.g., processes like a processor) program instructions.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A remote control apparatus provided with a manipulator, the remote control apparatus comprising:
   an end effector configured to display physical information, which varies according to an object making contact with a tip part, on a gauge display part;
   an endoscope configured to obtain an image of the tip part of the end effector and an image of the gauge display part; and
   a control part configured to control transmission of the image obtained by the endoscope, and to control operations of the tip part and the endoscope.

2. The remote control apparatus of claim 1, further comprising a display part configured to display an image being transmitted from the control part.

3. The remote control apparatus of claim 1, further comprising a first arm to which a connecting rod part of the end effector is connected, and a second arm to which the endoscope is connected,
   wherein the control part controls movements of the first arm and the second arm.

4. The remote control apparatus of claim 1, wherein the end effector comprises a first tip part and a second tip part that are configured to grip the object.

5. The remote control apparatus of claim 4, wherein at least one of the first tip part and the second tip part comprises:
   a body;
   a deformation member accommodated in the body and in which a fluid is filled;
   a contact member movably installed at the body, and configured to deform the deformation member in response to a force applied to the object at the time of making contact with the object; and
   a connection pipe connected between the deformation member and the gauge display part,
   wherein the fluid moves between the deformation member and the gauge display part through the connection pipe.

6. The remote control apparatus of claim 5, wherein the tip part further comprises an elastic member disposed inside the body and configured to provide the contact member with a restoring force.

7. The remote control apparatus of claim 5, wherein the gauge display part comprises:
   a cylinder connected to the connection pipe; and
   a piston disposed inside the cylinder and configured to reciprocate inside the cylinder in response to movement of the fluid.

8. The remote control apparatus of claim 7, wherein the gauge display part comprises:
   a position detection part configured to detect a position of the piston;
   a control part configured to convert the detected position into an electric signal; and
   an indicator configured to display the physical information in an electric manner according to a command by the control part.

9. A remote control apparatus comprising:
   a communication part configured to perform a communication with a manipulator;
   a control part configured to control such that an image being transmitted from the manipulator is displayed; and
   a console having an output part configured to display the image,
   wherein the image comprises an image of a tip part of an end effector and an image of gauge information of the end effector.

10. The remote control apparatus of claim 9, wherein the console is configured to transmit an operation control signal of the end effector to the manipulator.

11. The remote control apparatus of claim 9, wherein the console is configured to display an enlarged view of the image of the gauge information at a periphery of the image of the end effector.

12. A remote control apparatus provided with a manipulator, the remote control apparatus comprising:
   an end effector configured to display physical information, which varies according to an object making contact with a tip part, on a gauge display part,
   wherein the gauge display part and the tip part are constituent parts of the end effector.

13. The remote control apparatus of claim 12, further comprising: a connecting rod part connected to the tip part and configured to operate the tip part.

14. The remote control apparatus of claim 12, wherein the end effector further include a connecting rod part connected to the tip part and configured to operate the tip part.

15. The remote control apparatus of claim 12, further comprising:
   an endoscope configured to obtain an image of the tip part of the end effector and an image of the gauge display part.

* * * * *